(12) United States Patent
Hesketh

(10) Patent No.: US 9,956,139 B2
(45) Date of Patent: May 1, 2018

(54) PORTABLE CANISTER HOLDER WITH A COLLAPSIBLE BODY

(71) Applicant: Eric W. Hesketh, Peoria, AZ (US)

(72) Inventor: Eric W. Hesketh, Peoria, AZ (US)

(*) Notice: Subject to any disclaimer, the term of this patent is extended or adjusted under 35 U.S.C. 154(b) by 0 days. days.

(21) Appl. No.: 15/488,455

(22) Filed: Apr. 15, 2017

(65) Prior Publication Data

US 2017/0216140 A1    Aug. 3, 2017

Related U.S. Application Data

(63) Continuation of application No. 14/922,404, filed on Oct. 26, 2015, now abandoned, which is a continuation-in-part of application No. 14/102,405, filed on Dec. 10, 2013, now abandoned, which is a continuation-in-part of application No. 13/312,675, filed on Dec. 6, 2011, now abandoned.

(60) Provisional application No. 61/573,597, filed on Sep. 12, 2011.

(51) Int. Cl.
   *B60N 3/10*    (2006.01)
   *A61J 1/16*    (2006.01)
   *A61J 1/14*    (2006.01)

(52) U.S. Cl.
   CPC ........... *A61J 1/16* (2013.01); *A61J 1/1462* (2013.01); *B60N 3/102* (2013.01); *B60N 3/106* (2013.01)

(58) Field of Classification Search
   USPC ........ 211/71.04, 74, 77, 78; 248/311.2, 312, 248/312.1, 313, 102, 104, 106; 128/DIG. 6, 897
   See application file for complete search history.

(56) References Cited

U.S. PATENT DOCUMENTS

| | | |
|---|---|---|
| 1,634,162 A | 6/1927 | Tesk |
| 2,594,545 A | 4/1952 | Emens |
| 2,926,879 A | 3/1957 | Dietrich |
| 2,826,386 A | 3/1958 | Conrad |
| 2,893,675 A | 7/1959 | Smth et al. |
| 3,391,891 A | 7/1968 | Garden |
| 3,734,439 A | 5/1973 | Wintz |
| 3,970,344 A | 7/1976 | Baumann |
| 4,071,175 A | 1/1978 | Wagnon |
| 4,434,961 A | 3/1984 | Hoye |
| 4,773,348 A | 9/1988 | Rowley |
| 5,014,956 A | 5/1991 | Kayali |

(Continued)

*Primary Examiner* — Alfred Wujciak
(74) *Attorney, Agent, or Firm* — Lisa Foundation Patent Law Clinic at Arizona State University

(57) ABSTRACT

A portable canister holder is disclosed. The portable canister system comprises a collapsible substantially cylindrical, non-rigid body assembly comprising a plurality of vertical support rods configured to support a plurality of horizontal support restraints. The vertical support rods are able to pivot along with the horizontal supporting restraints, thereby collapsing the body assembly. The lowest horizontal support restraint further comprises a stopper to prevent the canister from being disconnected from the body assembly when in use. The portable canister holder further comprises an articulating joint member having a first end configured to attach to the body assembly and a second end configured to attach to a clamping device. The portable canister holder further comprises an IV holder configured to attach to the body assembly, the IV holder having a plurality of rods configured to support an IV bag.

12 Claims, 7 Drawing Sheets

(56) References Cited

U.S. PATENT DOCUMENTS

| | | | |
|---|---|---|---|
| 5,190,257 A | 3/1993 | Gradei et al. | |
| 5,342,009 A | 8/1994 | Lehner | |
| 6,045,017 A * | 4/2000 | Connell | A45F 5/02 |
| | | | 224/148.4 |
| 6,427,960 B1 | 8/2002 | Gehring et al. | |
| 6,513,449 B1 | 2/2003 | Stewart et al. | |
| 6,951,328 B1 | 10/2005 | Drapeau et al. | |
| 8,245,894 B2 | 8/2012 | Buehler | |
| 8,443,472 B2 * | 5/2013 | Sherman | A47C 21/00 |
| | | | 248/125.8 |
| 2009/0014611 A1 | 1/2009 | Hampton | |
| 2010/0230454 A1 | 9/2010 | Chinn et al. | |

* cited by examiner

PORTABLE CANISTER HOLDER WITH A COLLAPSIBLE BODY

CROSS REFERENCES TO RELATED APPLICATIONS

The present patent application is a continuation of and claims priority to U.S. patent application Ser. No. 14/922,404, titled "Portable Canister Holder with a Collapsible Body," filed on Oct. 26, 2015, which is a continuation-in-part of U.S. patent application Ser. No. 14/102,405, titled "Portable Canister Holder With A Collapsible Body," filed on Dec. 10, 2013, which is a continuation-in-part of U.S. patent application Ser. No. 13/312,675, titled "System and Method for a Portable Canister Holder with a Collapsible Body," filed on Dec. 6, 2011, which claims the benefit under 35 U.S.C. §119(e) of U.S. Provisional Application No. 61/573,597, filed Sep. 12, 2011, the disclosures of which are hereby incorporated by this reference in their entirety.

BACKGROUND OF THE INVENTION

Field of the Invention

The present invention relates to a portable canister holder capable of encasing an oxygen tank.

Description of Related Art

Some canister holders have been adapted to integrate a non-rigid collapsible body. Some canister holders have been adapted to include an attachment means such as a hook or clamp. Other canister holders have been adapted to include an intravenous (IV) holder. However, these systems do not teach the present invention. The known prior art does not include holders that feature an articulating joint designed to fit over objects of various sizes and shapes. Additionally, it does not appear that any prior art exists that teaches the invention in its entirety or suggests the combination of such.

So as to reduce the complexity and length of the Detailed Specification, and to fully establish the state of the art in certain areas of technology, Applicant(s) herein expressly incorporate(s) by reference all of the following materials identified in each numbered paragraph below.

U.S. Pat. No. 2,594,545 to Emens describes a nursing bottle holder with a "sliding" method of collapsibility with a curved yoke member. The invention does not teach the pivot method of collapsibility with a lower horizontal supporting restraint.

U.S. Pat. No. 2,826,386 to Conrad describes a nursing bottle holder with a ring meant to support the tapered end of a nursing bottle. The invention does not teach a stopper for supporting the base of a canister.

U.S. Publication No. 2009/0014611 to Hampton describes a drink holding device. The invention does not teach a method of collapsibility.

Applicant(s) believe(s) that the material incorporated above is "non-essential" in accordance with 37 CFR 1.57, because it is referred to for purposes of indicating the background of the invention or illustrating the state of the art. However, if the Examiner believes that any of the above-incorporated material constitutes "essential material" within the meaning of 37 CFR 1.57(c)(1)-(3), applicant(s) will amend the specification to expressly recite the essential material that is incorporated by reference as allowed by the applicable rules.

BRIEF SUMMARY OF THE INVENTION

The present invention provides among other things a portable canister holder. The portable canister holder has a collapsible, substantially cylindrical, non-rigid body assembly. The body assembly comprises one or more rods extending parallel to a vertical axis of the body assembly. The portable canister holder has one or more horizontal supporting restraints configured to enclose the canister within its perimeter and receive support from the plurality of vertical support rods. The vertical support rods are able to pivot along with the horizontal supporting restraints, thereby collapsing the body assembly. The one or more horizontal supporting restrains further comprise a lowest horizontal supporting restraint. The lowest restraint further comprises a stopper configured to prevent the canister from being disconnected from the body assembly during transport or use. The portable canister holder has an articulating joint with one end connected to the body assembly and another end connected to a clamping device or multiple clamping devices.

In the present embodiment, the horizontal supporting restraints are configured to adjust to enclose a plurality of different sized substantially cylindrical shaped objects. In the present embodiment, the horizontal supporting restraints have a circular shape. In other embodiments, the horizontal supporting restraints may have square or triangular shape. In the present embodiment, the horizontal supporting restraints are comprised of the same material as the body assembly. In other embodiments, the horizontal supporting restraints may be made with different materials such as metal, plastic, Velcro (hook and loop fasteners), or rubber. In the present embodiment, the portable canister holder comprises an IV holder. The IV holder is configured to attach to the body assembly or the articulating joint member. The IV holder has one or more rods configured to hold an IV dispensing device in place where at least one of the rods is configured with a hook.

The present invention provides among other things a portable canister holder. The invention has a collapsible, substantially cylindrical, non-rigid body assembly comprising one or more support rods extending parallel to a vertical axis of the body assembly. The present embodiment also features one or more restraints configured to enclose a canister within its perimeter. The restraint is coupled to one or more of the support rods. In the present embodiment, one of the restraints further comprises a stopper configured to prevent the canister from being disconnected from the body when in use.

In the present embodiment, the restraints are configured to adjust to enclose a plurality of different sized substantially cylindrical shaped objects. In the present embodiment, the restraints have a circular shape. In other embodiments, the restraints may have square or triangular shape. In the present embodiment, the restraints are comprised of the same material as the body assembly. In other embodiments, the restraints may be made with different materials such as metal, plastic, Velcro (hook and loop fasteners), or rubber. In the present embodiment, the portable canister holder comprises an IV holder. The IV holder is configured to attach to the body assembly or the articulating joint member. The IV holder has one or more rods configured to hold an IV dispensing device in place where at least one of the rods is configured with a hook.

The portable canister holder may be manufactured by configuring a one or more rods to fit around one or more restraints in a manner to form a collapsible, non-rigid body assembly capable of encasing a substantially cylindrical shaped object. The first end of an articulating joint may be attached to the body assembly. The second end of the articulating joint may be attached to a clamping device. An IV holder may be attached to the body assembly, the articulating joint, or a combination of the two. An IV holder may also be incorporated into the body assembly, whereby a telescopic rod may be extended to hold an IV dispensing device.

In the present embodiment, the horizontal supporting restraints are configured to adjust to enclose a plurality of different sized substantially cylindrical shaped objects. In the present embodiment, the horizontal supporting restraints have a circular shape. In other embodiments, the horizontal supporting restraints may have square or triangular shape. In the present embodiment, the horizontal supporting restraints are comprised of the same material as the body assembly. In other embodiments, the horizontal supporting restraints may be made with different materials such as metal, plastic, Velcro (hook and loop fasteners), or rubber. In the present embodiment, the portable canister holder comprises an IV holder. The IV holder is configured to attach to the body assembly or the articulating joint member. The IV holder has one or more rods configured to hold an IV dispensing device in place where at least one of the rods is configured with a hook.

Aspects and applications of the invention presented here are described below in the drawings and detailed description of the invention. Unless specifically noted, it is intended that the words and phrases in the specification and the claims be given their plain, ordinary, and accustomed meaning to those of ordinary skill in the applicable arts. The inventors are fully aware that they can be their own lexicographers if desired. The inventors expressly elect, as their own lexicographers, to use only the plain and ordinary meaning of terms in the specification and claims unless they clearly state otherwise and then further, expressly set forth the "special" definition of that term and explain how it differs from the plain and ordinary meaning. Absent such clear statements of intent to apply a "special" definition, it is the inventors' intent and desire that the simple, plain and ordinary meaning to the terms be applied to the interpretation of the specification and claims.

The inventors are also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the inventors are fully informed of the standards and application of the special provisions of pre-AIA 35 U.S.C. §112, ¶6 and post-AIA 35 U.S.C. §112(f). Thus, the use of the words "function," "means" or "step" in the Detailed Description or Description of the Drawings or claims is not intended to somehow indicate a desire to invoke the special provisions of 35 U.S.C. §112(f), to define the invention. To the contrary, if the provisions of 35 U.S.C. § 112(f) are sought to be invoked to define the inventions, the claims will specifically and expressly state the exact phrases "means for" or "step for, and will also recite the word "function" (i.e., will state "means for performing the function of [insert function]"), without also reciting in such phrases any structure, material or act in support of the function. Thus, even when the claims recite a "means for performing the function of . . . " or "step for performing the function of . . . " if the claims also recite any structure, material or acts in support of that means or step, or that perform the recited function, then it is the clear intention of the inventor not to invoke the provisions of 35 U.S.C. § 112(f). Moreover, even if the provisions of 35 U.S.C. § 112(f) are invoked to define the claimed inventions, it is intended that the inventions not be limited only to the specific structure, material or acts that are described in the preferred embodiments, but in addition, include any and all structures, materials or acts that perform the claimed function as described in alternative embodiments or forms of the invention, or that are well known present or later-developed, equivalent structures, material or acts for performing the claimed function.

BRIEF DESCRIPTION OF THE SEVERAL VIEWS OF THE DRAWINGS

A more complete understanding of the present invention may be derived by referring to the detailed description when considered in connection with the following illustrative figures. In the figures, like reference numbers refer to like elements or acts throughout the figures.

Elements and acts in the figures are illustrated for simplicity and have not necessarily been rendered according to any particular sequence or embodiment.

DETAILED DESCRIPTION OF THE INVENTION

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention. In many cases, a description of the operation is sufficient to enable one to implement the various forms of the invention, particularly when the operation is to be implemented in software. It should be noted that there are many different and alternative configurations, devices and technologies to which the disclosed inventions may be applied. The full scope of the inventions is not limited to the examples that are described below.

Those who require the assistance of bottled oxygen are left with the inconvenient task of finding a place to store the canister. Hospital staff and personnel often wrap these canisters in blankets or towels, and require the patient to keep the canister in their bed. In the case of infants, the canister is often placed in their crib. In other instances, the canister is left strapped to a cart, or dolly; however, these carts are expensive and require a surplus of storage space.

Hospitals cannot afford to purchase and store enough carts to meet the needs of every patient who requires oxygen. Moreover, even if a cart is available, the patient's room would require adequate space to house such a cart. This inhibits the space required to allow intravenous (IV) holders and other necessary machines. The present invention seeks to eliminate these burdens by providing an amicable solution for canister storage.

Figure 1:
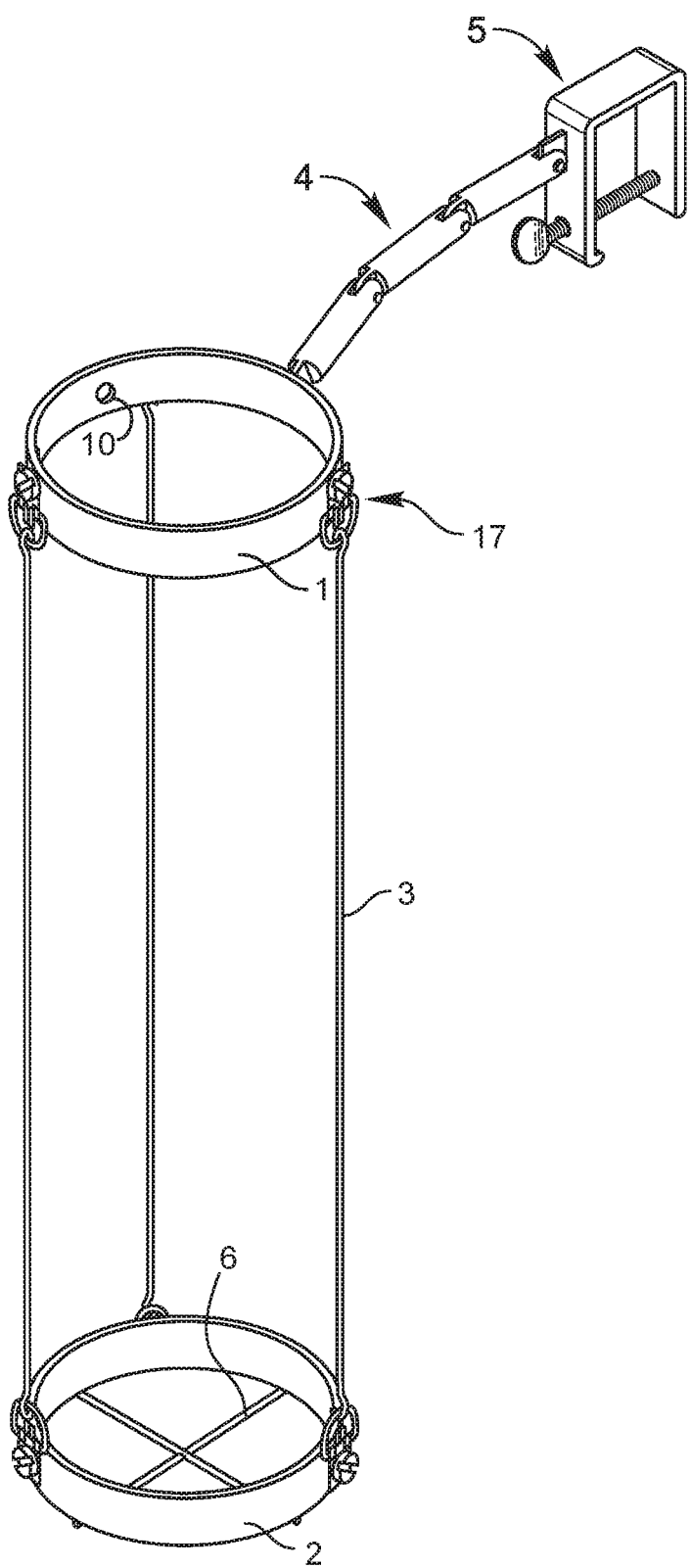
FIG. 1 depicts an implementation of a portable canister holder in use.
Figure 2:
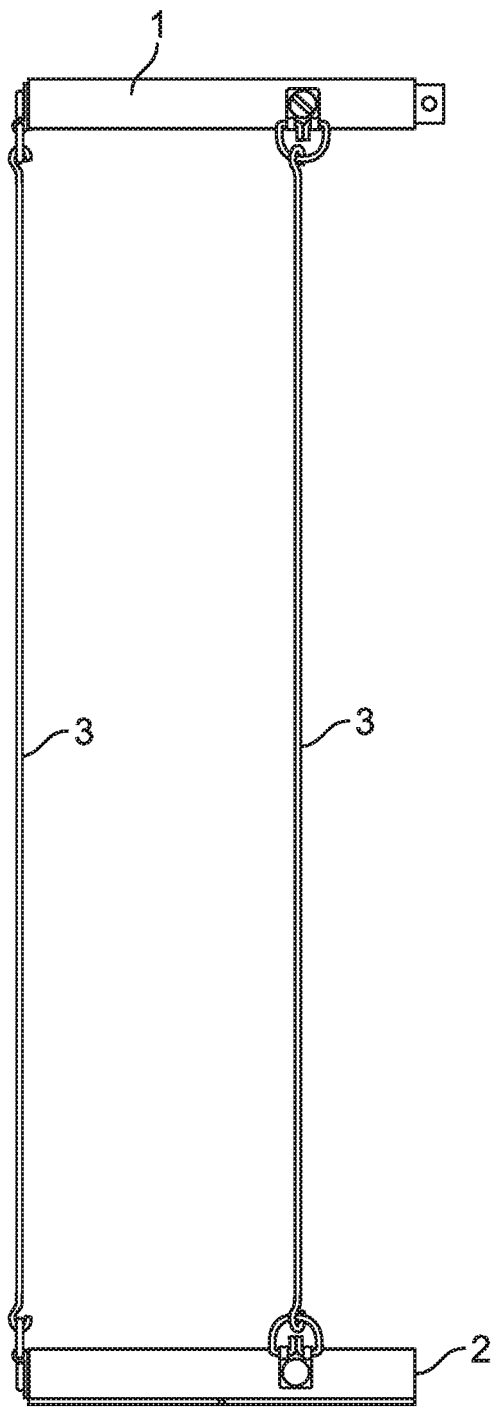
FIG. 2 depicts an implementation of a body assembly in use.
Figure 10:
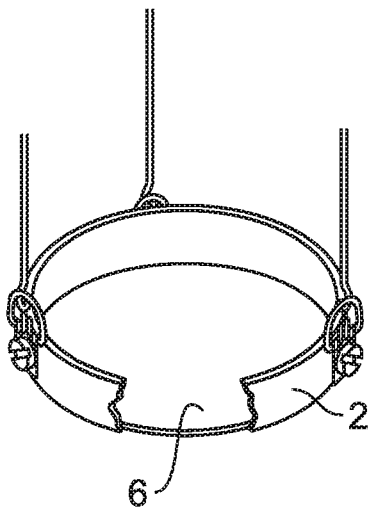
FIG. 10 depicts an implementation of a lower horizontal supporting restraint and stopper.
Figure 11:
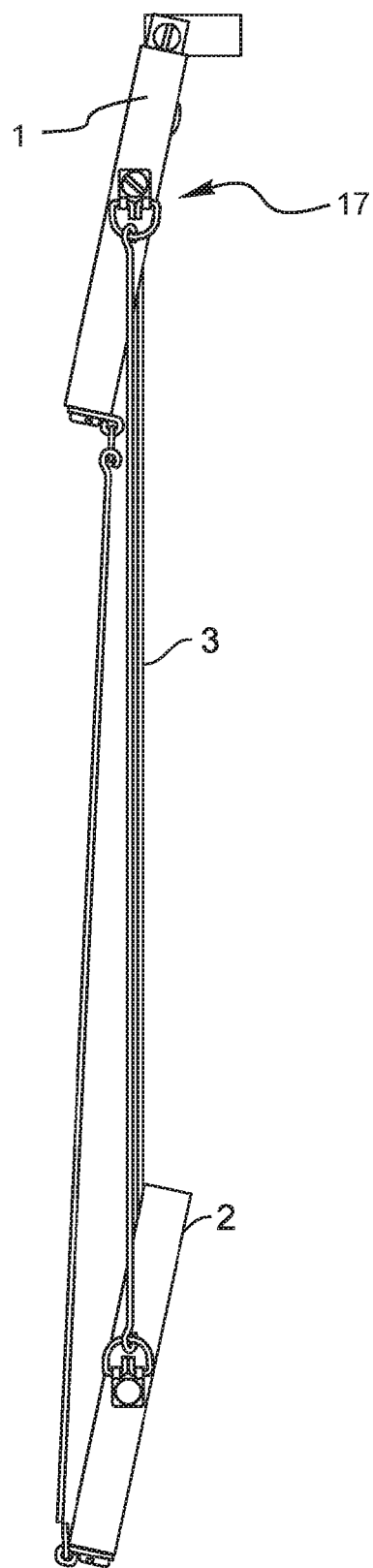
FIG. 11 depicts an implementation of a portable canister not in use, thereby in a collapsed state.

In the present embodiment, three vertical support rods 3 are configured to support two a highest horizontal supporting restraint 1 and a lowest horizontal supporting restraint 2 as shown in FIG. 1. The lower of these two horizontal supporting restraints 2 comprises a stopper 6 to prevent the canister from falling out of the bottom of the canister holder as shown in FIG. 1. In the present embodiment, the stopper comprises a set of smaller rods configured to form a brace as shown in FIG. 1. In other embodiments, the stopper may comprise a solid flat or curved plate, netting, or other configuration designed to stop the canister from falling out as shown in FIG. 10. In the present embodiment, when configured, the vertical support rods and the two horizontal supporting restraints are capable of pivoting with one another to form a collapsible, non-rigid body assembly as shown in FIG. 11. The vertical support rods and horizontal supporting restraints are coupled with a pivoting joint 17 as shown in FIG. 1. In the preferred embodiment, the vertical rods extend parallel to the vertical axis of the body assembly when stood upright as shown in FIG. 1. In other embodiments, the vertical rods may extend at an angle with respect to the vertical axis of the body assembly.

In the present embodiment, the horizontal support restraints are two substantially similarly sized circular rings 1, 2 configured in a manner such that they are substantially perpendicular to the vertical support rods as shown in FIG. 1. In other embodiments, the horizontal support restraints may take the form of other geometric shapes capable of encasing a substantially cylindrical shape. In other embodiments, the horizontal support restraints may be configured in a manner such that they are not substantially perpendicular to the vertical support rods. In other embodiments, the numbers of horizontal support restraints are not limited to two. In other embodiments, the horizontal restraints may be configured to encase various sized canister dimensions. For example, the horizontal restraints 1, 2 can be sized to fit canister diameters between about 2.5 inches and about 8 inches. In one embodiment, the horizontal restraints 1, 2, are sized to fit canister diameters of about 4.3 inches. Additionally, the vertical support rods 3 and the horizontal restraints 1, 2 can be configured to hold canisters between about 5 inches and about 45 inches in height.

In the present embodiment, the material used to make the vertical support rods 3 and the horizontal restraints 1, 2 comprises steel. In other embodiments, the material used to make the vertical support rods 3 and horizontal restraints 1, 2 may comprise plastic, carbon fiber, aluminum, or any other known material.

Figure 3:
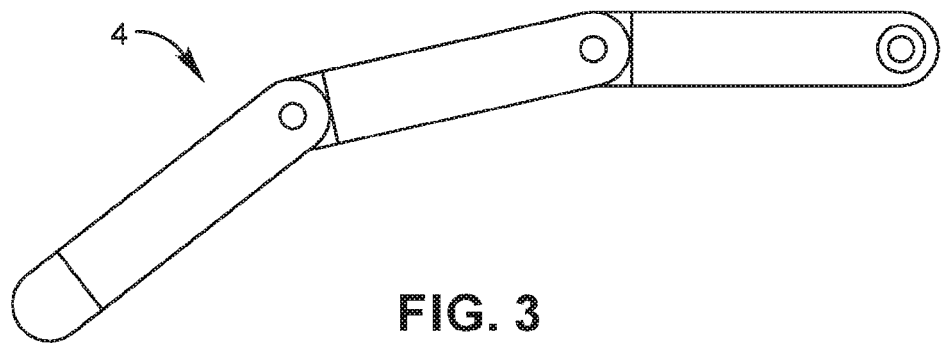
FIG. 3 depicts an implementation of an articulating joint.
Figure 4:
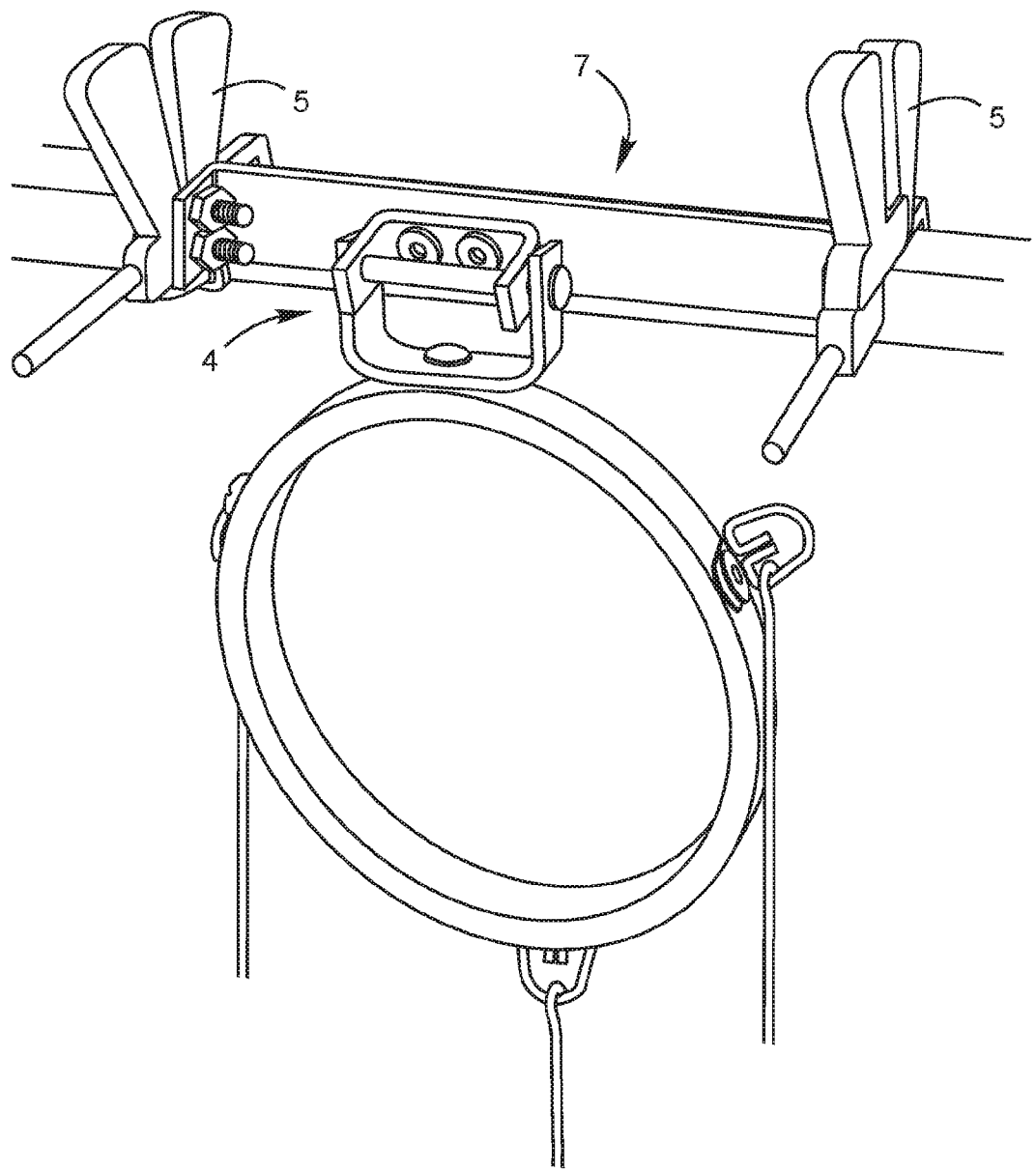
FIG. 4 depicts an implementation of an articulating joint while the canister holder is not in use.
Figure 5:
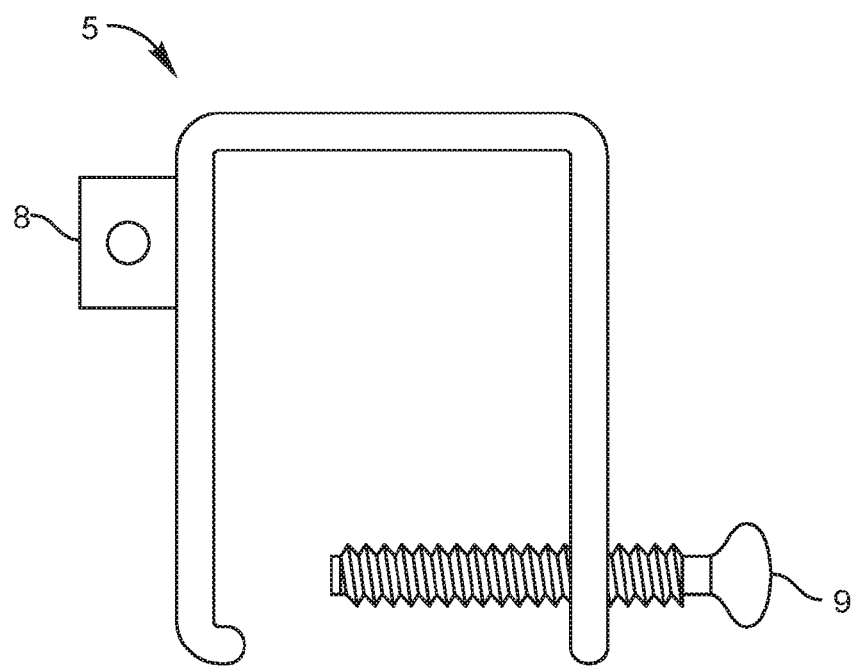
FIGS. 5-6 depict implementations of a clamping device.
Figure 6:
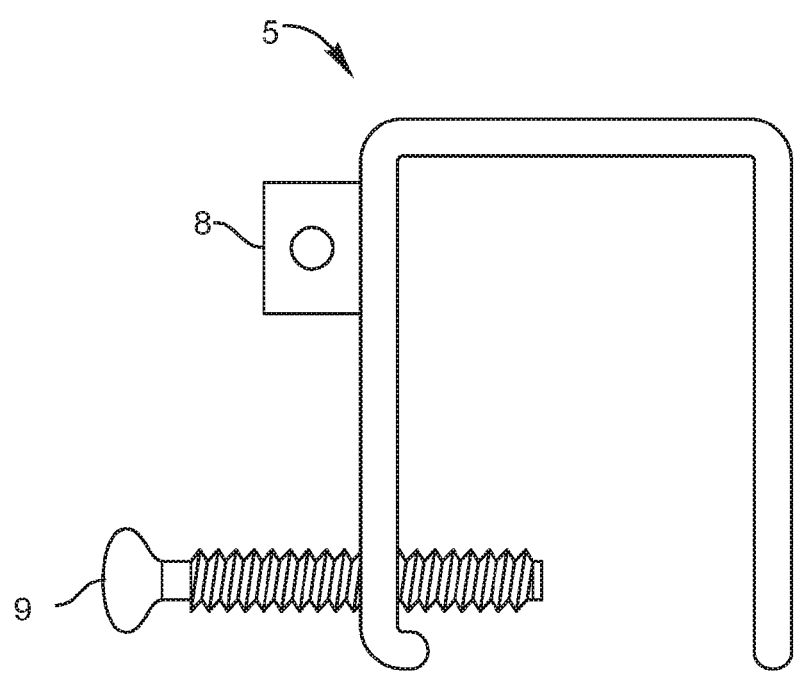

In the present embodiment, one end of an articulating joint 4 is coupled to the body assembly near the highest of the horizontal restraints 1 as shown in FIG. 1. In other embodiments, the articulating joint 4 may be coupled anywhere along the length of the body assembly. In the present embodiment, the second end of an articulating joint 4 is coupled a clamping device 5 as shown in FIG. 1. The clamping device 5 and the articulating joint 4 can be used to couple the portable canister holder, for example, to a patient bed or crib. As a result, a patient's oxygen tank or bottle (or any type of compressed gas cylinder) can be stored in the portable canister holder rather than inside the patient's bed or on a separate cart. The articulating joint 4 can be configured to fit the canister holder over objects of various sizes and shapes, such as bed rails. Alternately, the clamping device 5 can be configured to fit over objects of various sizes and shapes, such as bed rails. For example, when the canister holder is fit over a bed rail via the articulating joint 4 or the clamping device 5, the canister holder can hold an oxygen tank against the bedside or, when not holding an oxygen tank, lie flat against the bedside so as not to obstruct caregivers. In the present embodiment, the articulating joint is comprised of three articulating segments as shown in FIG. 3. In other embodiments, the articulating joint 4 may be comprised of one or more articulating segments. In other embodiments, the articulating joint 4 may be comprised of a single, multi-axial joint as shown FIG. 4. Additionally, in the present embodiment, the clamping device is a screw clamp 5 as shown in FIG. 5 and FIG. 6. In the present embodiment, the clamp has a joint connection 8 which couples to the articulating joint. In other embodiments, the clamping device may include other clamps such as spring clamp or C-clamps. In other embodiments, the clamping device may include more than one clamp 5 as shown in FIG. 4. The one of more clamps may be couple to the articulating joint by a joint bar 7.

Figures 7, 8:
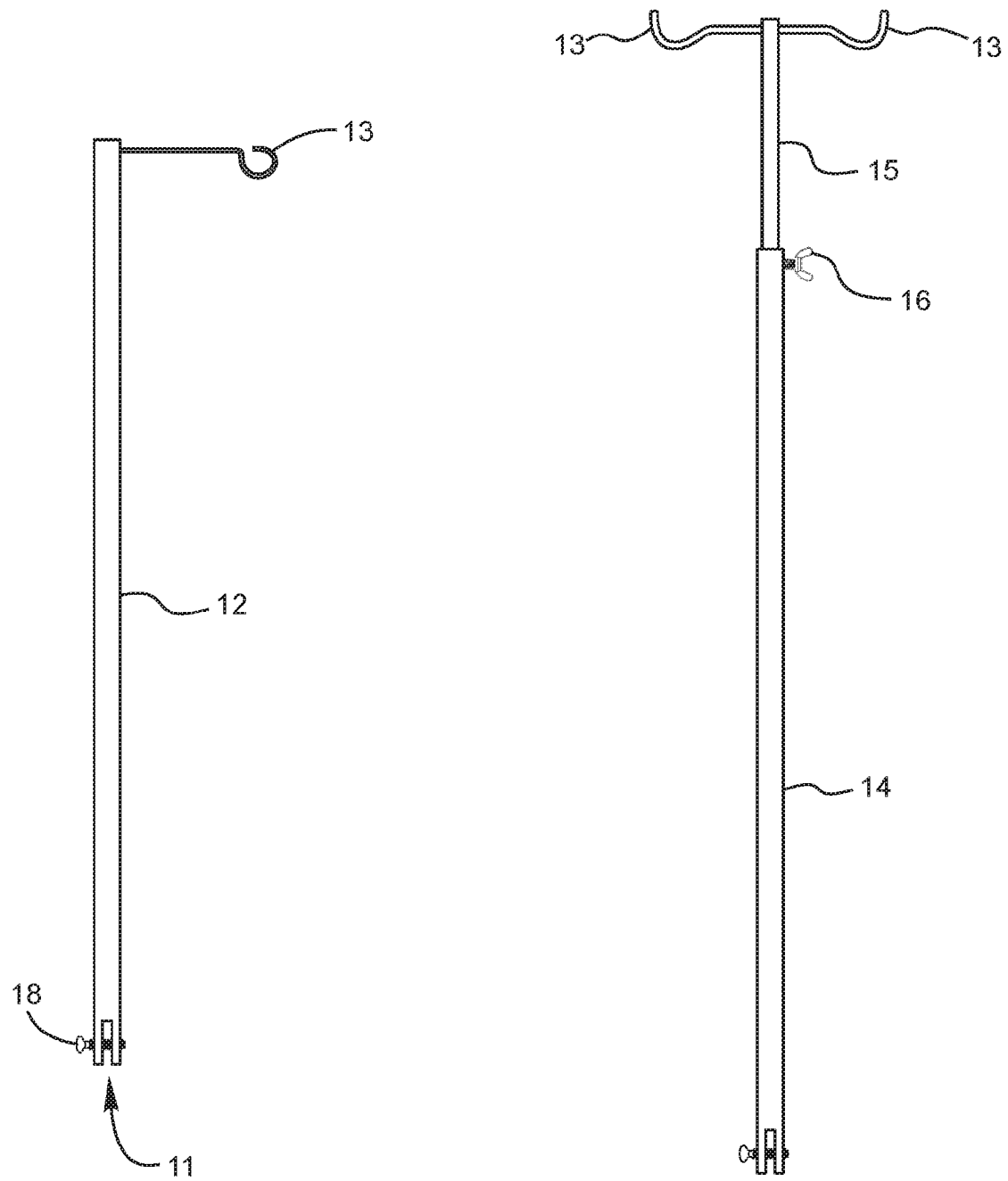
FIGS. 7-8 depict implementations of an IV holder.

In the present embodiment, an IV holder as shown in FIG. 7 and FIG. 8 is coupled to the body assembly near the higher horizontal restraint 1 as shown in FIG. 1. As a result, a patient's IV bags can be held up by the IV holder rather than a separate cart. Additionally, the IV holder, being a coupled to the patient's bed through the portable canister holder, can keep the patient's IV bags above the patient while the patient is being moved (rather than requiring the IV bags to be set on the patient or in the patient's bed). The IV holder may couple to the body assembly by sliding an IV notch 11 over the highest horizontal supporting restraint. The IV holder may be further coupled to the body assembly by tightening a fastener 18 as shown in FIG. 7, through an opening 10 in the higher horizontal supporting restraint as shown in FIG. 1. In the present embodiment, the IV holder comprises a vertical rod 12 as shown in FIG. 7 extending upwards in relation to the highest horizontal restraint 1. One end of the vertical rod is coupled to a hook 13 as shown in FIG. 7. In other embodiments, the IV holder may be coupled anywhere along the length of the body assembly, the articulating joint 4, or the clamping device 5. For example, the IV holder can be coupled to the articulating joint 4 or the clamping device 5 via the IV notch 11 and the fastener 18, or another clamping mechanism at the end of the vertical rod 12 or along the length of the vertical rod 12. In other embodiments, the IV holder may comprise a single rod or multiple rods with or without a hook capable of holding an IV bag. In other embodiments, the IV holder may comprise a telescopic rod 15 as shown in FIG. 8 that extends parallel from the vertical rod. In the present embodiment, the telescopic rod may be secured in place via an external locking mechanism. In other embodiments, the telescopic rod may be secured in place via an internal locking mechanism within the vertical rod.

Figure 9:
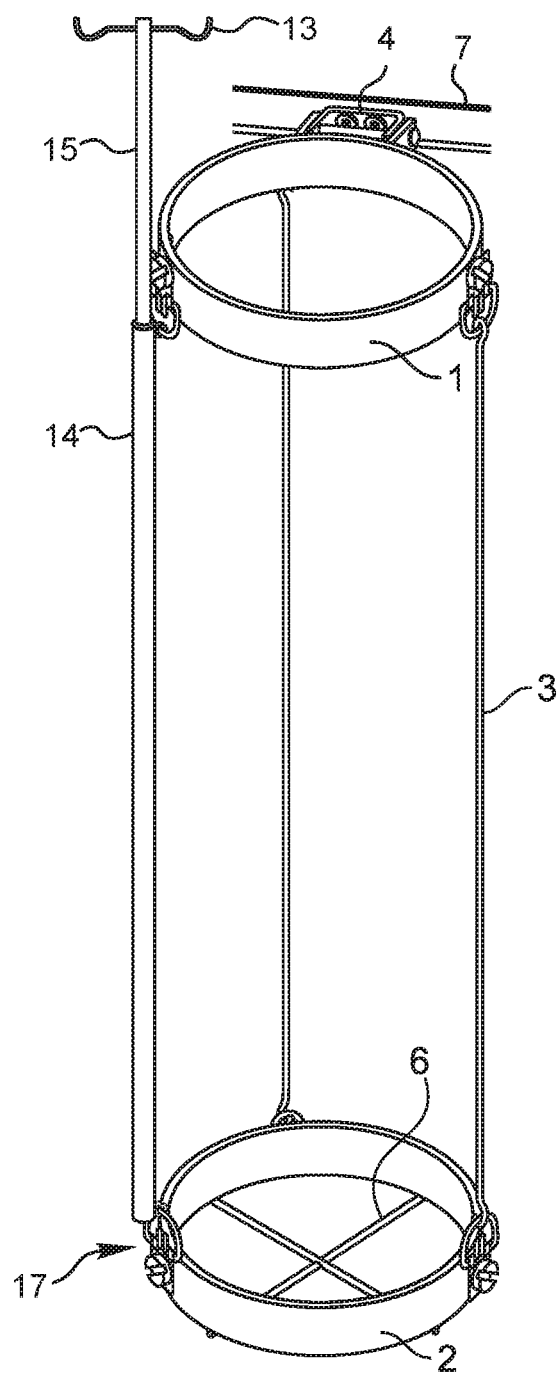
FIG. 9 depicts an implementation of a portable canister holder in use.

In the present embodiment, the IV holder may be attached to the body assembly in place of a vertical support rod as shown in FIG. 9. In the present embodiment, the vertical rod 14 is coupled to the pivoting joints 17 enabling the vertical rod to pivot with the horizontal supporting restraints 1 and 2.

I claim:

1. A portable canister holder, comprising:
    a collapsible substantially cylindrical, non-rigid body assembly, comprising:
        a plurality of vertical support rods extending parallel to a vertical axis of the collapsible substantially cylindrical, non-rigid body assembly;
        a plurality of restraints coupled to the plurality of vertical support rods, wherein the plurality of restraints are configured to enclose a canister within a perimeter of the plurality of restraints, at least one of the plurality of restraints further comprising a stopper configured to prevent the canister from escaping from the body assembly when the holder is in use, wherein the plurality of vertical support rods are configured to pivot with respect to the plurality of restraints;
    an articulating arm member having a first end, wherein the first end of the articulating arm member is configured to attach to at least one of the plurality of restraints; and
    an IV holder having a plurality of IV rods configured to hold an IV fluid dispensing device in place, wherein at least one of the vertical support rods from among the plurality of vertical support rods is comprised of the IV holder and the IV holder is further configured to couple to the collapsible substantially cylindrical, non-rigid body assembly.

2. The portable canister holder of claim 1, wherein the plurality of restraints are substantially horizontal.

3. The portable canister holder of claim 1, wherein the first end of the articulating arm member is coupled to one of the plurality of restraints.

4. The portable canister holder of claim 1, wherein the restraints have a substantially circular, substantially square, substantially rectangular, or substantially triangular shape.

5. The portable canister holder of claim 1, wherein the restraints are comprised of metal, plastic, hook and loop fasteners, or rubber.

6. The portable canister holder of claim 1, wherein the stopper is a flat plate, a curved plate, or netting.

7. The portable canister holder of claim 1, wherein the plurality of horizontal supporting restraints are each configured to encircle a canister diameter between about 2.5 inches and about 8 inches.

8. The portable canister holder of claim 1, wherein the plurality of horizontal supporting restraints and the plurality of vertical support rods are positioned relative to each other to hold a canister between about 5 inches and about 45 inches in height.

9. The portable canister holder of claim 1, wherein at least one of the plurality of IV rods is configured with a hook.

10. The portable canister holder of claim 1, wherein the articulating arm member comprises a second end coupled to a clamping device.

11. The portable canister holder of claim 10, wherein the clamping device comprises a screw clamp, spring clamp, or C-clamp.

12. The portable canister holder of claim 10, wherein the clamping device is configured to be coupled to a rail of a bed such that the collapsible substantially cylindrical, non-rigid body assembly holds the canister against the bed when holding the canister and lies flat against the bed when not holding the canister.

* * * * *